United States Patent [19]

Rogers et al.

[11] 4,443,543

[45] Apr. 17, 1984

[54] SEMIBATCH ETHANOL PRODUCTION

[75] Inventors: Peter L. Rogers, Northwood; David E. Tribe, Maroubra, both of Australia

[73] Assignee: Unisearch Limited, Kensington, Australia

[21] Appl. No.: 327,161

[22] Filed: Dec. 2, 1981

[30] Foreign Application Priority Data

Dec. 8, 1980 [AU] Australia ............................. PE6812

[51] Int. Cl.³ .............................................. C12P 7/06
[52] U.S. Cl. .................................. 435/161; 435/254; 435/813; 435/822
[58] Field of Search ........................ 435/161, 254–255, 435/172, 101, 813, 822

[56] References Cited

U.S. PATENT DOCUMENTS 3,406,114 10/1968 Goren ................................. 435/101

OTHER PUBLICATIONS

Rogers et al., "High Productivity Ethanol Fermentations with *Zymomonas mobilis*" *Process Biochemistry* Aug. 1, Sep. 1980, pp. 7–8 & 10.

Rogers et al., "Kinetics of Alcohol Production by *Zymomonas mobilis* at High Sugar Concentrations", *Chemical Abstracts,* vol. 91 (1979), Abstract No. 3905p.

Skotnicki et al., "Comparison of Ethanol Production by Different Zymomonas Strains", *Chemical Abstracts,* vol. 95 (1981), Abstract No. 5105j.

*Primary Examiner*—R. B. Penland
*Attorney, Agent, or Firm*—Murray & Whisenhunt

[57] ABSTRACT

A process for the production of ethanol from a carbohydrate substrate such as glucose comprising culturing a flocculant strain of *Zymomonas mobilis* such as ATCC 31822, in a semi-batch manner periodically allowing the flocculent cells to settle, removing the ethanol containing supernatant and introducing fresh fermentation medium into the fermentor.

6 Claims, 1 Drawing Figure

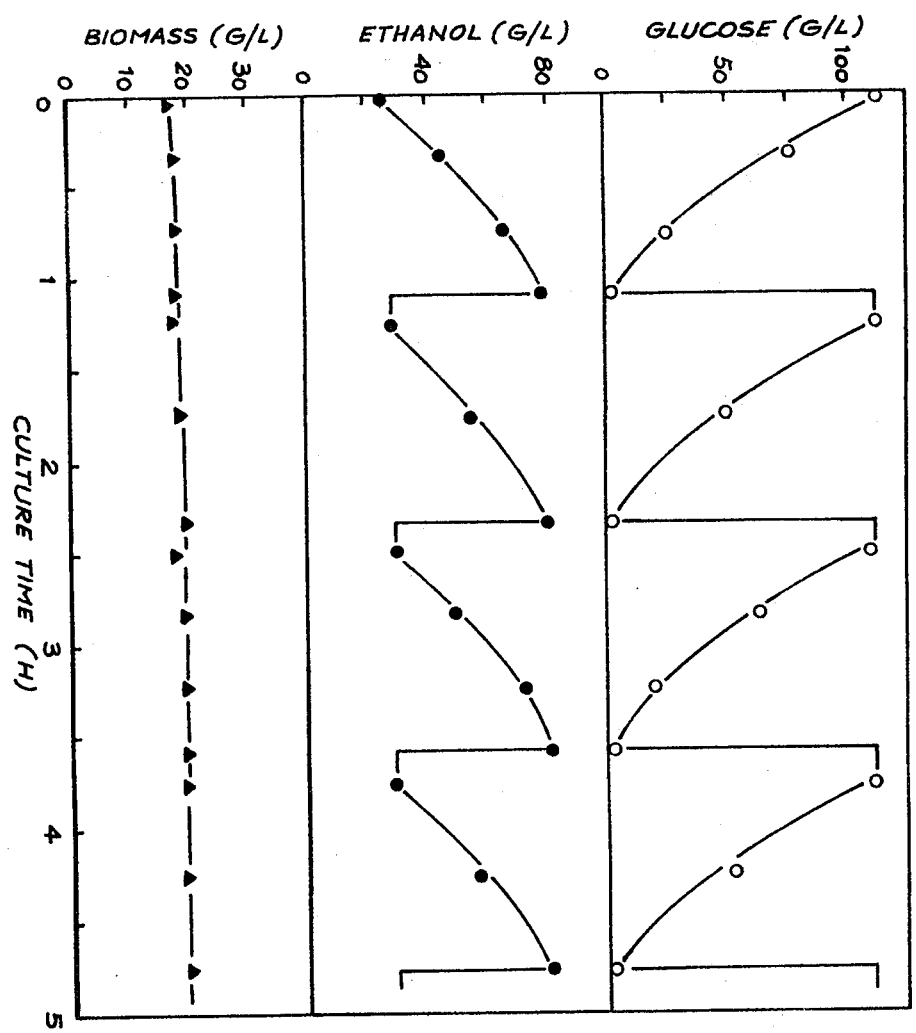

SEMIBATCH ETHANOL PRODUCTION

The present invention relates to a process for the production of ethanol from fermentable substrates using selected strains of the bacterium *Zymomonas mobilis*.

Conventionally fermentable substrates such as the simple sugars are fermented to produce ethanol using yeasts. It is also known that certain bacteria including *Zymononas mobilis* can also ferment suitable substrates. The present inventors have disclosed in copending application Ser. No. 240,099 details of certain preferred strains of *Zymomonas mobilis* which show higher rates of specific ethanol productivity and higher ethanol tolerance levels than other known strains of *Zymomonas mobilis*. These improved strains of *Zymomonas mobilis* may be used in batch or continuous fermenters or in semibatch fermenters. In a semibatch fermenter repeated withdrawals are made of supernatant liquid containing ethanol and at least a proportion of the bacterial cells are left in the fermenter which is then recharged with a substrate solution and the process repeated. In semibatch processes it is highly desirable to retain in the fermenter as many of the bacterial cells as is possible. The present inventors have discovered that flocculent strains of *Zymomonas mobilis* can be developed which settle rapidly in the fermenter allowing a high proportion of supernatant to be withdrawn while leaving a majority of the cells in the fermenter.

The present invention consists in a process for the production of ethanol from a medium containing glucose or another carbohydrate fermentable by *Zymomonas mobilis*, comprising culturing in the medium in a semibatch manner a flocculent strain of *Zymomonas mobilis*, periodically allowing the flocculent cells to settle, removing the ethanol containing supernatant and introducing fresh fermentation medium into the fermenter.

The flocculent strains provide a rapid and low cost technique for the settling of *Zymomonas mobilis* cells in the fermenter, so that when the supernatant containing the ethanol is withdrawn the cells are retained for further fermentation. For present purposes the term "flocculent strain" is intended to mean a strain of microorganism which naturally forms aggregates of 100 cells or more under normal growth conditions. The advantage of using a flocculent strain is that the majority of cells are maintained during these repeated withdrawals. Further advantages lie in the fact that sterile conditions are readily maintained and no expensive equipment is required for cell concentration external to the fermenter and for cell recycle. As batch culture is currently widely practised by the fermentation industry it is likely that semibatch culture will be an attractive option for process improvement and is likely to occur before continuous fermentation techniques are introduced.

The preferred strain of *Zymomonas mobilis* is a flocculent strain (ATCC 31822) derived by a mutation and selection program from strain CP4 (ATCC 31821) described in the foregoing patent specifications. This flocculent strain (ATCC 31822) shows the advantageous characteristics of CP4 (ATCC 31821) in terms of ethanol productivity and tolerance while showing strong flocculent characteristics.

In the process according to this invention an initial charge of fermentation medium is inoculated with the bacteria and the medium maintained to cause the bacteria to multiply. The medium is gently agitated to circulate the bacteria through the medium. This latter process is aided by the carbon dioxide which is evolved during the fermentation process. When fermentation is completed and no more carbon dioxide is being evolved the agitator is turned off and the colonies of flocculent cells allowed to settle. The ethanol containing supernatant is then removed and replaced by a fresh charge of fermentation medium. The ethanol contained in the removed supernatant is recovered by distillation or another of the conventional techniques for ethanol recovery.

The supernatant renamed preferably comprises from 60 to 90% of the total volume of the fermentation medium.

The preferred carbohydrates for use as fermentable substrates in the culture medium include, in addition to glucose, simple sugars such as fructose and sucrose, and starch or cellulose hydrolysates. It will be recognised that any one strain of *Zymomonas mobilis* may not ferment all of these substrates and therefore from any particular substrate a suitable, flocculent strain may be selected.

EXPERIMENTAL RESULTS

Using a flocculent strain of *Zymomonas mobilis*, ZM401 (ATCC 31822), a series of semi-batch fermentations have been carried out. The results presented represent a combination of a relatively high ethanol level (80 g/l) together with a relatively high volumetric productivity for the fermenter (50 g/l/h). This compares with an ethanol concentration of 80 g/l and a fermenter productivity of 12 g/l/h for a flocculent yeast (*Saccharomyces uvarum*).

The experimental conditions for the semi-batch fermentation of *Zymomonas mobilis* were as follows:
Organism: *Zymomonas mobilis* ZM401 (ATCC 31822)
Growth Medium: 150 g/l glucose, 10 g/l yeast extract (Oxoid), 1 g/l $(NH_4)_2SO_4$, 1 g/l $KH_2PO_4$, 0.5 g/l $MgSo_4 7H_2O$
Environmental conditions: pH=5.0, T=30° C.
Fermenter working volume: 2 liters
Fraction of fermenter working volume replaced each semi-batch operation: 0.7

The results of the experiment which illustrate the achievement of both relatively high ethanol levels and a relatively high productivity are shown in FIG. 1. It was found that between 95% and 99% of the *Z. mobilis* cells were retained in the fermenter after removal of the supernatant.

Further strain development will involve the development of ethanol-tolerant mutants, for example *Zymomonas mobilis* ZM481 (ATCC 31823), which are also flocculent and this will lead to further process improvements. Such improvements are claimed also in this patent.

Flocculent strains may be obtained by mutating an existing strain of *Z. mobilis* such as by treatment with nitrosoguanadine and selection of those mutant strains showing the fastest settling rates.

We claim:

1. A process for the production of ethanol from a medium containing glucose or another carbohydrate fermentable by *Zymomonas mobilis*, comprising fermenting in the medium in a continuous, semibatch or batch manner flocculent *Zymomonas mobilis*, ATCC 31822 which forms aggregates of 100 cells or more under the fermenting conditions, periodically allowing the flocculent cells to settle, removing the ethanol containing supernatant and introducing fresh fermentation medium into the fermenter.

2. A process as claimed in claim 1 in which the fermentable carbohydrate is selected from the group consisting of glucose, fructose, sucrose and other simple sugars; starch or cellulose hydrolysates; and mixtures thereof.

3. A process as claimed in claim 1 in which the supernatant removed comprises from 60 to 90% of the total volume of the fermentation medium.

4. A process as claimed in claim 1, in which fermentation is in a continuous manner.

5. A process as claimed in claim 1, in which fermentation is in a semibatch manner.

6. A process as claimed in claim 1, in which fermentation is in a batch manner.

* * * * *